(12) United States Patent
Schuetz

(10) Patent No.: US 6,206,566 B1
(45) Date of Patent: Mar. 27, 2001

(54) X-RAY APPARATUS FOR PRODUCING A 3D IMAGE FROM A SET OF 2D PROJECTIONS

(75) Inventor: Oliver Schuetz, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/211,347

(22) Filed: Dec. 15, 1998

(30) Foreign Application Priority Data

Nov. 2, 1998 (DE) .............................................. 198 50 494

(51) Int. Cl.[7] .......................................................... A61B 6/03
(52) U.S. Cl. .............................................. 378/205; 378/62
(58) Field of Search ................................ 378/4, 196, 197, 378/198, 205, 62, 63, 901

(56) References Cited

U.S. PATENT DOCUMENTS

| | | | |
|---|---|---|---|
| 5,706,324 | 1/1998 | Wiesent et al. ........................ | 378/4 |
| 6,023,495 | * 2/2000 | Adler et al. ........................... | 378/4 |
| 6,028,907 | * 2/2000 | Adler et al. ........................... | 378/4 |
| 6,049,582 | * 4/2000 | Navab ................................... | 378/4 |
| 6,050,724 | * 2/2000 | Schmitz et al. ....................... | 378/62 |

* cited by examiner

*Primary Examiner*—David P. Porta
*Assistant Examiner*—Drew A. Dunn
(74) *Attorney, Agent, or Firm*—Schiff Hardin & Waite

(57) ABSTRACT

An X-ray apparatus has an X-ray examination system with an X-ray source and an X-ray detector which can be displaced relative to a subject for the pickup of 2D projections, an arrangement for determining extrinsic and intrinsic imaging parameters, and having a control and computing means stage for reconstructing 3D images from the 2D projections using the extrinsic and intrinsic imaging parameters. The arrangement for determining the intrinsic imaging parameters includes X-ray-positive marks which are allocated to the X-ray source and which are substantially in one plane and in the path of an X-ray beam emanating from the X-ray source.

13 Claims, 3 Drawing Sheets

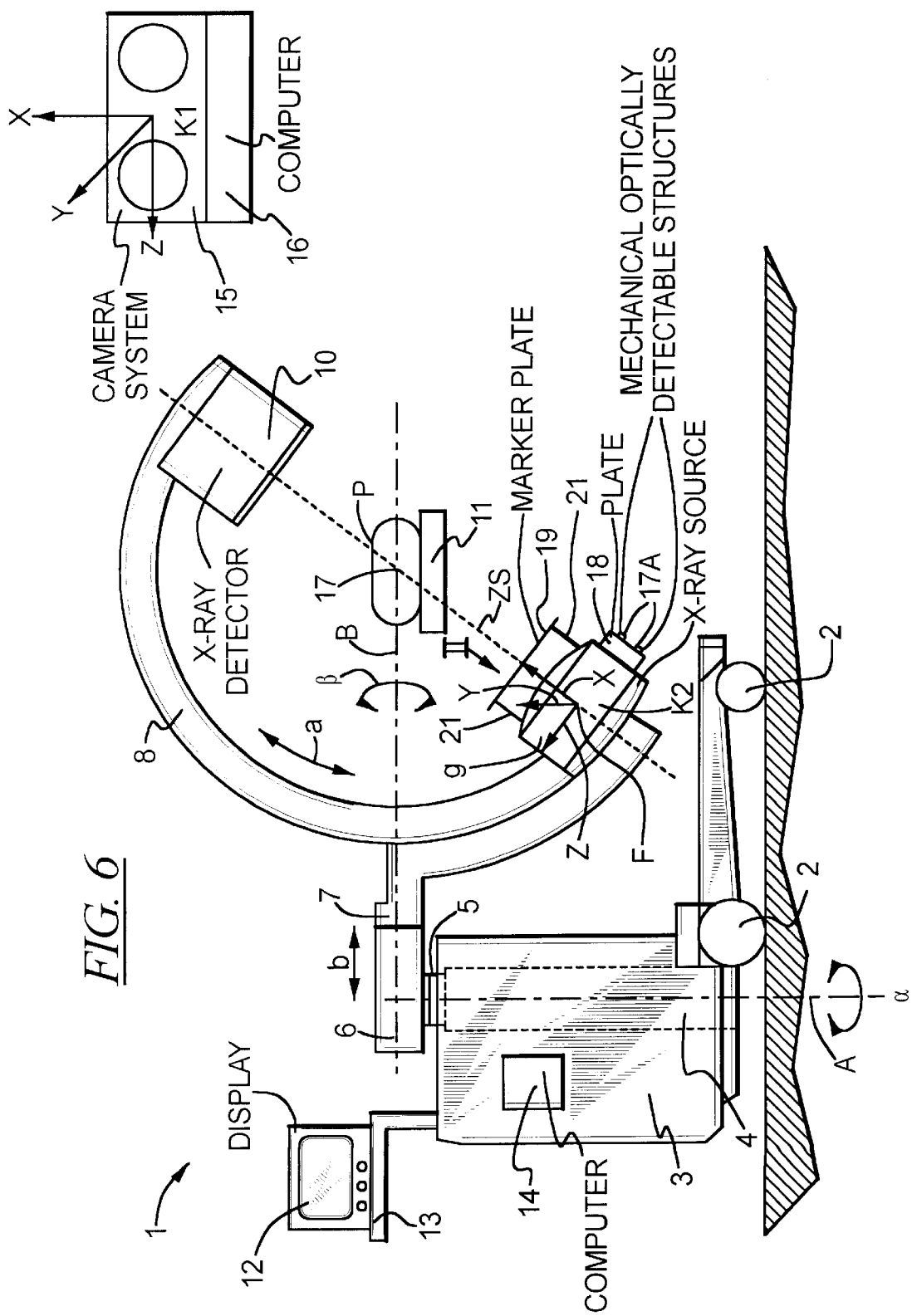

X-RAY APPARATUS FOR PRODUCING A 3D IMAGE FROM A SET OF 2D PROJECTIONS

BACKGROUND OF THE INVENTION

1. Field of the Invention

The present invention relates to an X-ray apparatus of the type having an X-ray examination system which with an X-radiation source and an X-ray detector which can be displaced relative to an examination subject for the pickup of 2D projections of a region of the subject, with subsequent reconstruction of 3D images of the region of the subject.

2. Description of the Prior Art

X-ray apparatuses of the above type commonly have a C-arm for mounting the X-ray source and the X-ray detector, the C-arm being mounted in a holding device such that it can be displaced in motorized fashion along its perimeter in a defined angle range (orbital motion). To obtain 2D projections from various projection angles for the reconstruction of 3D images—of a body region of a living organism, for example—in the pickup of the 2D projections of the body region of the organism, the C-arm is displaced along its perimeter subsequent to corresponding placement relative to the living organism to be examined. 3D images of the body region of the organism are subsequently reconstructed from the 2D projections captured with the X-ray examination system during the displacing motion. The reconstruction of 3D images is preconditioned by the precise knowledge of the projection geometries, i.e. the knowledge of the positions and orientations of the X-ray source and of the X-ray detector with respect to a stationary coordinate system during each of the individual 2D projections.

It has proven problematic that known stationary C-arm X-ray apparatuses, and quite particularly mobile C-arm X-ray devices, exhibit mechanical instabilities, particularly with respect to the displacement of the C-arm along its perimeter, so that the actual displacing motion of the X-ray examination system deviates from the ideal displacing motion due to deformations of the C-arm. Thus, the precision in the reproducibility of the projection geometries which is necessary for a reconstruction of 3D images cannot be achieved, particularly with the known mobile C-arm X-ray devices, for which reason additional position detection systems are necessary in order to be able to determine the projection geometries in every 2D projection. The following two methods are known for determining the projection geometries:

a) German OS 195 12 819 (corresponding to U.S. Pat. No. 5,706,324) teaches the utilization of a marker ring, usually made of plexiglass with inserted metal structures, which is arranged around the body region of the examined organism. The metal structures of the marker ring are visible in the 2D projections of the examined body region, so that the respective projection geometries of the 2D projections can be calculated from their position. This method has the disadvantage that the marker ring has a relatively large diameter, so that the distance between the X-ray source and the marker ring is very small (a few centimeters), particularly given mobile C-arm X-ray devices having a relatively small C-arm. The metal structures are thus imaged with significant enlargement in the 2D projections, so that large parts of the 2D projections are covered by the metal structures. Furthermore, only a small region of the metal structures of the marker ring is imaged in the 2D projections, so that the determination of the projection angle with the aid of the low number of imaged metal structures is difficult.

b) Gauging measurements are performed prior to the actual patient measurement, under the assumption that the system behavior, i.e. essentially the displacement of the C-arm, is largely reproducible. This method is very time-consuming and can be used only given mechanically reinforced stationary C-arm X-ray devices. Application in mobile X-ray devices is impossible, due to the previously mentioned mechanical instabilities of such X-ray devices, mechanical stabilzation being out of the question for mobile X-ray devices due to the large weight increase, which restricts mobility.

SUMMARY OF THE INVENTION

It is an object of the present invention to provide an X-ray apparatus of the abovementioned type wherein the determination of the projection geometries is simplified and is suitable not only for a stationary X-ray apparatus but also for a mobile apparatus.

This object is inventively achieved in an X-ray apparatus with an X-ray examination system including an X-ray source and an X-ray detector which can be displaced relative to a subject for the pickup of 2D projections, with means for determining extrinsic and intrinsic imaging parameters, i.e. for determining the projection geometries of the X-ray system in each 2D projection, and with control and computing means for reconstructing 3D images from the 2D projections with the aid of the extrinsic and intrinsic imaging parameters, wherein the means for determining the intrinsic imaging parameters include X-ray-positive marks which are allocated to the X-ray source and which are arranged, substantially in one plane, in the path of an X-ray beam emanating from the X-ray source, the geometric positions of the marks relative to each other and to the X-ray source being known. For determining the projection geometries in each 2D projection, means for determining extrinsic imaging parameters and means for determining intrinsic imaging parameters are thus provided. The extrinsic imaging parameters describe the position and orientation of the focus of the X-ray source as a reference point, or the position and orientation of an arbitrarily selected zero point of the detector surface of the X-ray receiver as a reference point, for example, in a first stationary coordinate system. The intrinsic imaging parameters specify the geometric relation between the X-ray source and the X-ray detector—i.e., the distance of the X-ray source and the X-ray detector from one another, the orientation of the X-ray source and of the X-ray detector relative to one another, and the displacement of the X-ray detector perpendicular to the axis of the center beam of an X-ray beam emanating from the X-ray source, for example—in a second coordinate system, whose origin is preferably located at the reference point, i.e. at the focus of the X-ray source or at the zero point of the detector surface, for example. The position of the origin and the orientation of the second coordinate system—whose origin is located at the focus of the X-ray source, for example, and which, like the marks, is displaced relative to a subject together with the X-ray source in various 2D projections—is specified, for every 2D projection, by the extrinsic imaging parameters, as already noted.

In the examination of a subject, for each 2D projection of the subject, a matrix I of the intrinsic imaging parameters and a matrix E, which contains the extrinsic imaging parameters, are determined, whereby, according to P=I*E, a projection matrix P results for each 2D projection, each projection matrix P comprising the projection geometries of the corresponding 2D projection which are necessary for the reconstruction of 3D images. The projection matrices, which the control and computing means calculate from the extrinsic and intrinsic imaging parameters, are used for the reconstruction of 3D images from the 2D projections.

The means for determining the extrinsic imaging parameters are operable independent of the means of the intrinsic imaging parameters, so that the determination of the extrinsic and intrinsic imaging parameters is possible separately and thus is simplified in relation to the evaluated signals. The intrinsic imaging parameters are obtained using the X-radiation, with X-ray-positive marks which are arranged in one plane being allocated to the X-ray source such that they are imaged in the 2D projections. Since the geometric positions of the marks relative to each other and to the X-ray source are known in the second coordinate system, for example, whose origin is situated at the focus of the X-ray source, the intrinsic imaging parameters—i.e., the distance between the X-ray source and the X-ray detector, the orientation of the X-ray source relative to the X-ray detector, and a potential displacement of the X-ray detector perpendicular to the axis of the center beam of the X-ray beam emanating from the X-ray source—can be determined in simple fashion by the control and computing means, for example, using the distance relations of the marks, imaged in the 2D projections, relative to each other. It is particularly advantageous in the determination of the intrinsic imaging parameters that no additional sensor analysis is required at the X-ray apparatus. Furthermore, because the measurement ensues at precisely the same time as the pickup of a 2D projection, the phenomenon known as measurement jitter (the time difference, which is problematic for the evaluation of the signals, between the measurement of the 2D projection and the measurement of the intrinsic imaging parameters) does not occur.

According to a variation of the invention, the means for determining the extrinsic imaging parameters include a plate, which is arranged at the X-ray source or at the X-ray detector outside the path of the X-ray beam and which carries detectable structures or detectable optically active elements, and a stationary camera system which cooperates with the plate. The plate is preferably arranged at the X-ray source in a geometrically specific fashion and preferably carries infrared light sources, whose positions can be detected by the camera system, as detectable optically active elements, for example. At least for the examination of a subject, the camera system is arranged in a geometrically specific fashion relative to the X-ray system, in the first stationary coordinate system. Using the camera images of the infrared light sources of the plate, which are picked up during a displacing motion of the X-ray system relative to a subject, the exact position of the plate—and thus, for example, of the focus of the X-ray source, which is simultaneously the origin of the second coordinate system—can be determined in the first stationary coordinate system. The detection of the individual positions of the focus of the X-ray source in the course of an examination can ensue by a separate computer which is a component of the means for determining the extrinsic imaging parameters, or by the control and computing means of the X-ray apparatus. Known image analysis methods can be used for the evaluation of the camera images.

In a particularly preferred embodiment of the invention the X-ray-positive marks are arranged in an X-ray-transparent marker plate which is allocated to the X-ray source such that it is penetrated by the X-ray beam in 2D pickups. The substantially planar marker plate is preferably arranged directly at the X-ray source and in the path of the X-ray beam emanating form the X-ray source. The distance between the marker plate and the focus of the X-ray source is about 200 mm. The marker plate thus always is located outside the work area of persons active at the X-ray means, and it does not limit the X-ray means in its functionality in any way. The exact position of the marks contained in the marker plate relative to the focus of the X-ray source, the positions of the marks in the second coordinate system, can be determined by a one-time calibration measurement with a calibrating cap on the marker plate. Furthermore, the geometric positions of the marks in the marker plate are known from the construction data for the production of the marker plate.

According to a variation of the invention, the marker plate carries at least three marks, which are arranged in the marker plate such that they can be imaged in different image corners or at different image margins of the 2D projections. In this way, the central tissue region of an examination subject to be imaged in the 2D projection is not superimposed by the imaged marks. Rather, the imaged marks are located in regions of a 2D projection which are usually less relevant for the diagnosis.

According to a further variation of the invention, the marks are of a spherical or rod-shaped design, resulting in clearly recognizable and evaluatable images of the marks in the 2D projections.

In another embodiment of the invention the X-ray source has a diaphragm which defines the cross-section of the X-ray beam and which has edges, the edges in the 2D projections representing the image margin, and the edges of the diaphragm fulfilling the function of linear marks. The advantage of this embodiment of the invention is that marks need not be additionally added to the X-ray apparatus and arranged in the path of the X-ray beam for the determination of the intrinsic imaging parameters; rather, an already existing structure of the X-ray apparatus, namely the diaphragm of the X-ray source, i.e., the edges of the diaphragm, serve as such marks. Since the positions of the edges of the diaphragm, which are situated substantially in one plane, relative to each other and to the focus of the X-ray source, i.e., their positions in the second coordinate system, are known or can be detected in a one-time calibrating process, the intrinsic imaging parameters can be determined with the aid of the imaging relations of the imaged edges, which can also be derived from the 2D projections, or the corner points formed by these edges.

According to another variation of the invention, the edges of the diaphragm can be provided with structures which can be imaged in the 2D projections. The structures can be spherical structures attached to the edges of the diaphragm, or of cutouts in the edges of the diaphragm.

DESCRIPTION OF THE DRAWINGS

FIG. 6 is a side view of an inventive x-ray apparatus in an embodiment employing mechanical structures as optically detectable items.

DESCRIPTION OF THE PREFERRED EMBODIMENTS

Figure 1:
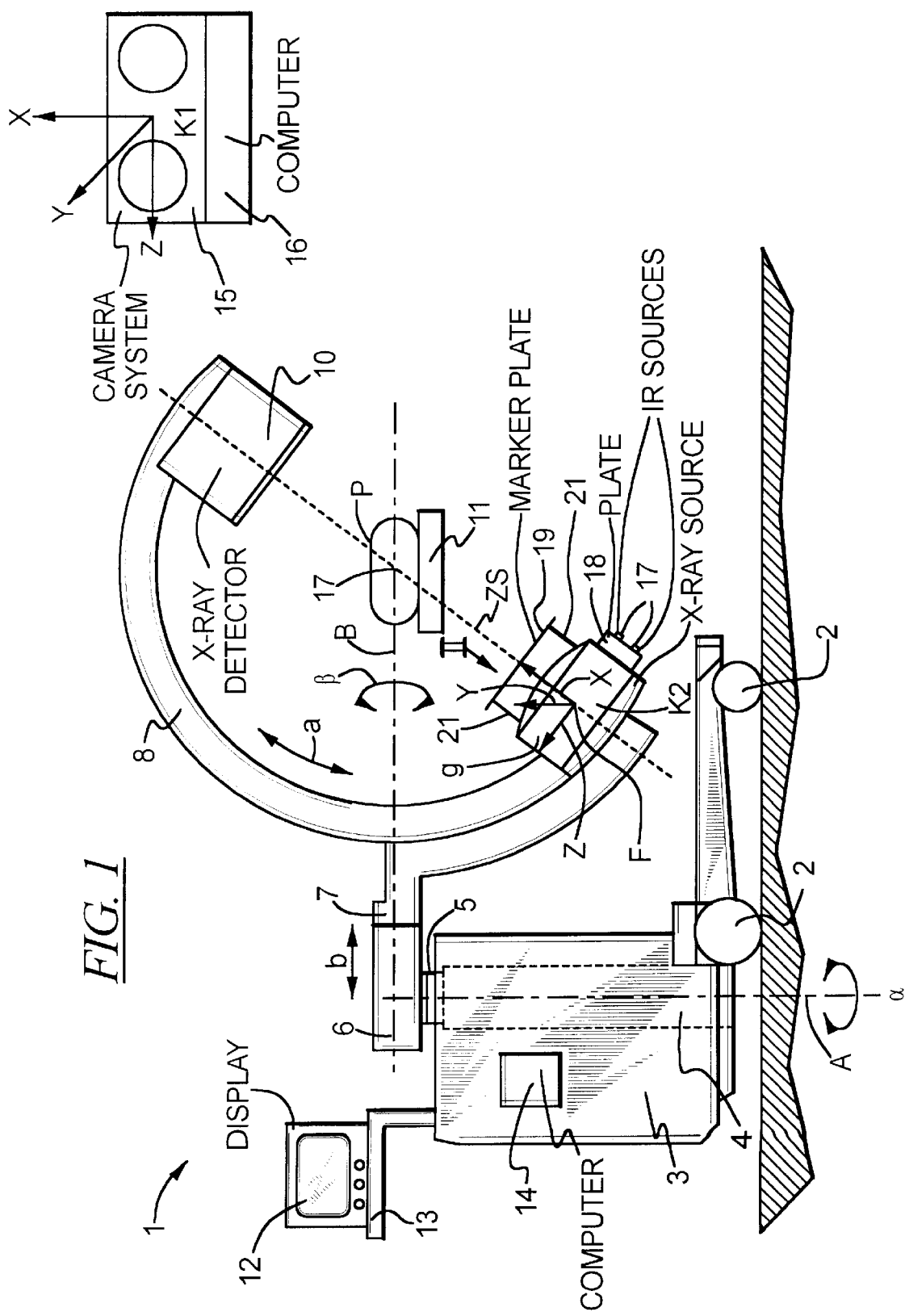
FIG. 1 is a side view of an inventive X-ray apparatus in an embodiment employing IR sources as optically detectable items.

In an exemplary embodiment, the inventive X-ray apparatus depicted in FIG. 1 is a C-arm X-ray device 1 with a device cart 3 that can be driven on wheels 2. The C-arm X-ray device 1 has a lifting device 4, which is depicted in FIG. 1 only schematically, with a column 5 having a longitudinal axis A around which the column 5 can be rotated in the direction of the double arrow α. A holder 6 is arranged at the column 5, a mount 7 being in turn arranged at the holder 6 for mounting a C-arm 8, which has an isocenter IZ. The C-arm 8 carries an X-ray source 9 and an X-ray detector 10, which are disposed opposite each other at the respective ends of the C-arm 8 and which are arranged relative to one another such that a center beam ZS, emanating from the X-ray source 9, of an X-ray beam proceeds through the isocenter IZ of the C-arm 8 and strikes the X-ray receiver 10 approximately in the middle. The C-arm 8 is mounted at the mount 7 such that it can be displaced along its perimeter in motorized fashion in the direction of the double arrow a, in a manner not depicted. The mount 7 is mounted at the holder 6 such that it is rotatable about a common axis B of the holder 6 and the mount 7 (cf. double arrow β, angulation) and displaceable in the direction of the axis B (double arrow b). The C-arm 8, which is connected to the column 5 of the lifting device 4 via the mount 7 and the holder 6, can be displaced vertically relative to the device cart 3 with the aid of the lifting device 4.

In the exemplary embodiment, the C-arm X-ray device 1 is provided for the creation of 3D images of a body region of a patient P, depicted only schematically in FIG. 1, who is lying on a patient bed 11. The 3D images are reconstructed from 2D projections of the body region from different angles which are obtained with the aid of the X-ray examination system, which is comprised of the X-ray source 9 and the X-ray detector 10, and the images can be displayed on a display device 12 arranged on a holder 13 of the C-arm X-ray device 1.

To pick up the 2D projections from various projection angles, the C-arm 8, which carries the X-ray examination system, is displaced in motorized fashion along its perimeter, in the direction of the double arrow a, through an angle range greater than 180° around the examined and displayed body region of the patient P. Approximately 50 to 100 2D projections of the body region of the patient P are picked up with the X-ray system from different angles of projection during the displacing motion.

The reconstruction of 3D images from the 2D projections ensues with control and computing means of the X-ray device 1 in the form of an efficient computer 14. The computer 14 not only performs the reconstruction of 3D images, but also controls the motorized displacing motion of the C-arm 8 and the pickup of 2D projections by the X-ray examination system. The computer 14 can be a multiprocessor system which permits parallel calculations, which shorten the calculation time. The computer 14 need not necessarily be integrated in the C-arm X-ray device 1, but can be constructed as an external computer which is correspondingly connected to the C-arm X-ray device 1.

As stated above, for the reconstruction of 3D images from 2D projections, the precise knowledge of the projection geometries, i.e., knowledge of the positions and the orientations of the X-ray source 9 and of the X-ray detector 10, is required for each 2D projection. The projection geometries can be expressed in intrinsic and extrinsic imaging parameters.

In the exemplary embodiment, the extrinsic imaging parameters specify the position and the orientation of the focus F of the X-ray source 9—as the origin of a second coordinate system K2, which is moved together with the X-ray source 9—in a stationary coordinate system K1, whose position and orientation is defined in the exemplary embodiment by the means for determining the extrinsic imaging parameters. The selection of the coordinate system K1 is arbitrary; i.e., the origin and the orientation of the coordinate system K1 can be defined differently.

In the exemplary embodiment of FIG. 1, the means for determining the extrinsic imaging parameters include a camera system 15 (which comprises at least two cameras), a computer 16, and a plate 18, which is provided with an infrared light source 17 and is arranged at the X-ray source 9. The camera system 15, which can pick up infrared signals, is arranged in a geometrically specific fashion in the stationary coordinate system K1, at least during an examination procedure. The camera system 15 is oriented with respect to the C-arm X-ray device 1 such that all motions of the C-arm 8 are conducted within its field of view. The camera system 15 thus can visually detect the infrared signals emitted by the infrared light sources 17 during a displacing motion of the C-arm 8 along its perimeter. As shown in FIG. 6, optically detectable mechanical structures 17A alternatively can be used. The evaluation of the camera images picked up during the displacing motion of the C-arm 8 is undertaken by the computer 16. Using the camera images, the computer 16 calculates the respective positions and orientations of the plate 18 in relation to the first coordinate system K1. These data are made available to the computer 14 of the C-arm X-ray device 1 by the computing means 16 via signal lines (not depicted in FIG. 1) or telemetrically. Since the plate 18 is arranged in a geometrically specific fashion relative to the X-ray source 9, or to the focus F of the X-ray source 9, the computer 14 using this data can always detect the current position of the focus F of the X-ray source 9, and thus the position of the origin of the second coordinate system K2, in each 2D projection. For every 2D projection, this results in a matrix E which contains the extrinsic imaging parameters of the respective 2D projection. The matrices E with the extrinsic imaging parameters for the various 2D projections are respectively set up in real time.

In the exemplary embodiment depicted in FIG. 1, the intrinsic imaging parameters—which specify the distance of the X-ray source 9 from the X-ray detector 10, the orientation of the X-ray source 9 relative to the X-ray detector 10, and a possible displacement of the X-ray detector 10 perpendicular to the axis of the center beam ZS of the X-ray beam emanating from the X-ray source 9—are detected using a marker plate 19. The marker plate 19 is arranged directly at the X-ray source 9, specifically in the path of an X-ray beam which emanates from the X-ray source 9. In the exemplary embodiment, the marker plate 19, which is constructed of an X-ray-permeable material such as plexiglass, is provided with four X-ray-positive spherical marks 20. The marks 20 are arranged in the marker plate 19 such that they are situated in different image corners or at different image margins of the 2D projections that are picked up with the aid of the X-ray detector 10. In this way, the body regions of an examined patient P which are imaged in the 2D projections are not superimposed by the imaged marks 20'. Should the imaged marks 20' prove disturbing in the 2D projections, the imaged marks 20' can subsequently be calculated out of the 2D projections in an image processing step on the basis of the position and size of the imaged marks 20', which are known from the intrinsic imaging parameters, and on the basis of the known X-ray absorption of the marks 20.

In the exemplary embodiment, the determination of the intrinsic imaging parameters from the marks 20', imaged in the 2D projections, occurs with reference to the second coordinate system K2, whose origin is situated at the focus F of the X-ray source 9. The positions of the marks 20 are known, or can be detected with a one-time calibration process, in the second coordinate system K2. The relative positions of the marks 20 in the marker plate 19 are also known from the construction data of the marker plate 19. The evaluation of the 2D projections is made by the computer 14, which determines the intrinsic imaging parameters using the known geometric positions of the marks 20 in the second coordinate system K2 and the distance relations of the imaged marks 20' in the 2D projections. This is accomplished by means of suitable pattern detection. Thresholding methods, cross-correlation, template matching and segmenting methods, such as are known and used in imaging analysis, are possible methods. For each 2D projection, the intrinsic imaging parameters are combined in a matrix I in real time. A projection matrix P is ultimately obtained, in real time, from the matrices E and I for each 2D projection. The projection matrices P are used for the reconstruction of 3D images by the computer 14.

Figure 2:
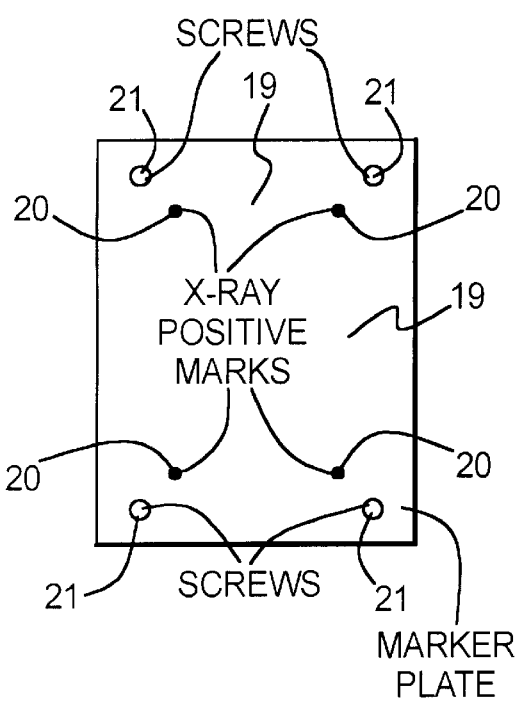
FIG. 2 is a view, as seen in the direction of arrow II in FIG. 1, of the marker plate of the X-ray apparatus from FIG. 1.
Figure 3:
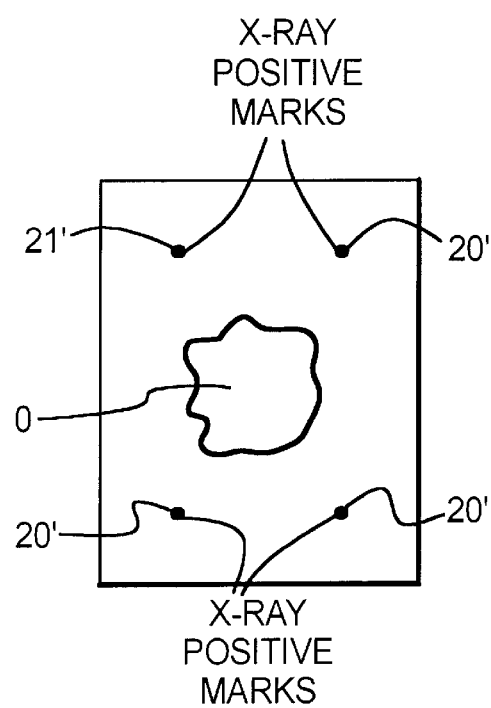
FIG. 3 shows a 2D projection with imaged marks of the marker plate from FIG. 2.

FIG. 2 shows the marker plate 19 from FIG. 1, which is provided with the marks 20, in the direction of the arrow 11 in FIG. 1. In the exemplary embodiment, the marker plate 19 is fastened to the X-ray source 9 with screws 21. The marker plate 19 can also be fastened to the X-ray source 9 by means of clamps or other suitable fixing elements. FIG. 3 depicts the marks 20' of the marker plate 19 that are imaged in the corners of a 2D projection and that are not superimposed on an imaged subject O.

In the exemplary embodiment, the plate 18 of the means for determining the extrinsic imaging parameters is arranged at the X-ray source 9. However, the plate 18 can also be arranged at the X-ray detector 10. In this case, it is appropriate to place the origin of the second coordinate system K2, with reference to which the intrinsic imaging parameters are specified, at an arbitrarily selectable reference point of the X-ray detector 10, which can be the midpoint of the detector surface of the X-ray detector 10, for example. The origin of the second coordinate system K2 need not necessarily be located on or in the detector surface, however. The origin of the second coordinate system K2 can also be clearly defined given such an arrangement of the plate 18 at the X-ray detector 10. In this case, as in the manner described above, the intrinsic imaging parameters can be determined using the distance relations of the marks 20' which are imaged in the 2D projections, it being possible to derive these relations using the 2D projections and to define them with reference to the second coordinate system K2, with the geometric positions of the marks 20 in the marker plate 19, which is allocated to the X-ray source 9, relative to each other and relative to the X-ray source 9, or to the focus F of the X-ray source 9, being known.

Furthermore, the plate 18 need not necessarily carry infrared light sources 17. Rather, the plate 18 can be provided with mechanical structures or other elements, preferably optically active elements, which enable the position determination of the plate 18 with the aid of camera images.

Beyond this, the marks 20 need not necessarily be arranged in a marker plate 19. The marks 20 need only be allocated to the X-ray source 9 such that they are located in the path of an X-ray beam which emanates from the X-ray source 9 and are substantially situated in one plane, whereby their positions relative to each other are known or can be detected easily.

Beyond this, instead of spherical marks, rod-shaped marks or differently shaped marks which can be imaged clearly in X-ray images can be used for the determination of the intrinsic imaging parameters.

Figure 4:
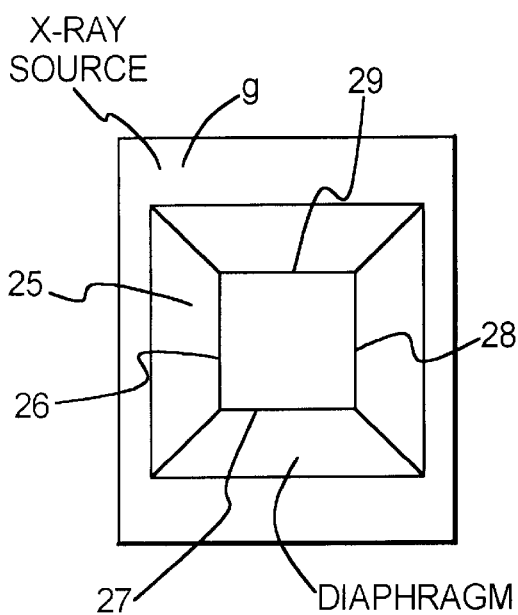
FIG. 4 illustrates an X-ray source from FIG. 1, with a diaphragm.

FIG. 4 depicts an illustration of the X-ray source 9 from FIG. 1 as seen in the direction of the arrow 11 from FIG. 1, whereby the marker plate 19 has been removed from the X-ray source 9. A diaphragm 25 of the X-ray source 9, which is present in each X-ray source per se, is further detailed in FIG. 4. The diaphragm 25 serves to limit the cross-section of the X-ray beam emanating from the X-ray source 9 such that only such X-ray quanta as can strike at the detector surface of the X-ray detector 10 leave the X-ray source 9. The edges 26 to 29 of the diaphragm 25 are imaged in the 2D projections and form the image margin. In the exemplary embodiment, the edges 26 to 29 of the diaphragm 25, which are imaged in the 2D projections, are applied in the determination of the intrinsic imaging parameters, the imaged edges 26 to 29 serving the function of linear marks. Since the edges 26 to 29 are situated substantially in one plane, and the geometric positions of the edges 26 to 29 of the diaphragm 25 relative to one another are known, and the relative positions of the edges 26 to 29 in the second coordinate system K2—which, in the case of the exemplary embodiment, has its origin at the focus F of the X-ray source 9—can also be detected without difficulty, in a calibrating procedure. For example, the intrinsic imaging parameters can also be determined with the aid of the distance relations of the edges 26 to 29 of the diaphragm 25, which are imaged in the 2D projections. The advantage of this embodiment of the invention is that additional X-ray-positive marks need not be provided at the X-ray source 9 in order to be able to determine the intrinsic imaging parameters. The comers in the 2D projections formed by the edges 26 to 29 can be used for the evaluation, for example.

Figure 5:
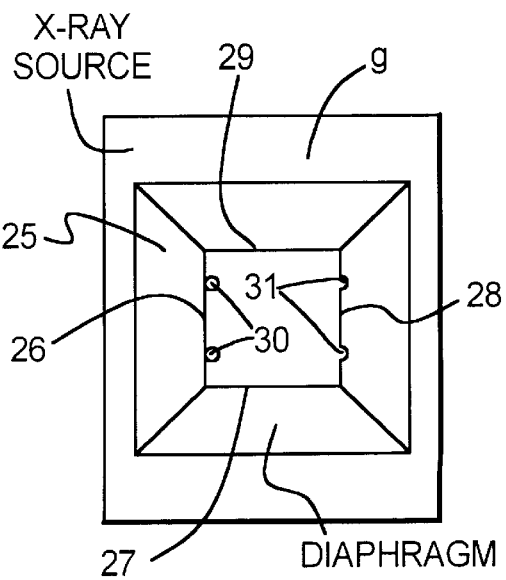
FIG. 5 illustrates an X-ray source from FIG. 1, with a diaphragm provided with structures that can be imaged.

As depicted in FIG. 5, the edges 26 to 29 of the diaphragm 25 can be provided with additional structures that can be imaged, such as X-ray-positive marks 30 or detectible cutouts 31, It being possible to use these for the determination of the intrinsic imaging parameters as prominent points in the 2D projections.

The evaluation of the 2D projections comprising the imaged edges 26 to 29 of the diaphragm 25, or structures 30, 31, ensues analogously in the manner described above.

The exemplary embodiments depicted in the figures and described above can be employed for the determination of the intrinsic imaging parameters either alternatively to each other or in combination.

The invention has been described on the basis of the example of a C-arm X-ray device 1, however, the invention is not limited to use in mobile C-arm X-ray devices, but is also usable in stationary X-ray devices.

Although modifications and changes may be suggested by those skilled in the art, it is the intention of the inventor to embody within the patent warranted hereon all changes and modifications as reasonably and properly come within the scope of his contribution to the art.

I claim as my invention:

1. An X-ray apparatus comprising:
   an X-ray examination system having an X-ray source which emits an X-ray beam from a focus and an X-ray detector on which said X-ray beam is incident;

means for rotating said X-ray examination system around an examination subject while irradiating said examination subject with said X-ray beam from a plurality of different projection angles for obtaining a plurality of 2D projection images of said examination subject respectively as said plurality of different projection angles, each of said 2D projection images having a unique projection geometry associated therewith;

means for determining extrinsic imaging parameters and means for determining intrinsic imaging parameters for each of said 2D projection images, said extrinsic imaging parameters identifying a geometric reference point of said X-ray examination system for each of said 2D projection images and said intrinsic imaging parameters identifying a geometric relation between said X-ray source and said X-ray detector for each of said 2D projection images, and means for determining the respective projection geometries for said 2D projection images from said extrinsic imaging parameters and said intrinsic imaging parameters, said means for determining intrinsic imaging parameters comprising a plurality of X-ray positive marks disposed substantially in one plane and in a path of said X-ray beam, said X-ray positive marks being disposed at respective geometric positions relative to each other and relative to said X-ray source which are known; and a computer using said 2D projection images and said projection geometries for constructing a 3D image therefrom of said examination subject.

2. An X-ray apparatus as claimed in claim 1 wherein said means for determining extrinsic imaging parameters include a plate mounted on said X-ray examination system outside of said path of said X-ray beam, said plate carrying a plurality of optically detectable items, and a stationary optical camera having a field of view containing said plate.

3. An X-ray apparatus as claimed in claim 2 wherein said optically detectable items comprise a plurality of optically detectable structured components on said plate.

4. An X-ray apparatus as claimed in claim 2 wherein said optically detectable items comprise a plurality of optically active elements mounted on said plate.

5. An X-ray apparatus as claimed in claim 1 further comprising a marker plate on which said X-ray positive marks are disposed, said marker plate being transparent to X-rays and being disposed relative to said X-ray source so that said plate is penetrated by said X-ray beam during irradiation of said examination subject from said plurality of different projection angles.

6. An X-ray apparatus as claimed in claim 5 wherein said marker plate comprises at least three of said X-ray positive marks, said at least three X-ray positive marks being disposed on said marker plate so as to be present at respectively different image corners of each of said 2D projection images.

7. An X-ray apparatus as claimed in claim 6 wherein said at least three marks each has a spherical shape.

8. An X-ray apparatus as claimed in claim 6 wherein said at least three marks each has a rod shape.

9. An X-ray apparatus as claimed in claim 5 wherein said marker plate comprises at least three of said X-ray positive marks, said at least three X-ray positive marks being disposed on said marker plate so as to be present at respectively different image margins of each of said 2D projection images.

10. An X-ray apparatus as claimed in claim 9 wherein said at least three marks each has a spherical shape.

11. An X-ray apparatus as claimed in claim 9 wherein said at least three marks each has a rod shape.

12. An X-ray apparatus as claimed in claim 1 further comprising a diaphragm attached to said X-ray source in said path of said X-ray beam, said diaphragm limiting a cross-section of said X-ray beam and having diaphragm edges, said diaphragm edges defining image margins in each of said 2D projection images, said diaphragm edges fulfilling the function of linear marks.

13. An X-ray apparatus as claimed in claim 12 wherein said diaphragm edges each have a structure which is distinctively imaged in each of said 2D projection images.

* * * * *